US011154342B2

(12) United States Patent
Wahl

(10) Patent No.: US 11,154,342 B2
(45) Date of Patent: Oct. 26, 2021

(54) WEDGE PLATES AND METHODS OF USE

(71) Applicant: Wright Medical Technology, Inc., Memphis, TN (US)

(72) Inventor: Rebecca H. Wahl, Escondido, CA (US)

(73) Assignee: Wright Medical Technology, Inc., Memphis, TN (US)

( * ) Notice: Subject to any disclaimer, the term of this patent is extended or adjusted under 35 U.S.C. 154(b) by 0 days.

(21) Appl. No.: 16/069,924

(22) PCT Filed: Mar. 23, 2016

(86) PCT No.: PCT/US2016/023721
§ 371 (c)(1),
(2) Date: Jul. 13, 2018

(87) PCT Pub. No.: WO2017/164861
PCT Pub. Date: Sep. 28, 2017

(65) Prior Publication Data
US 2019/0008569 A1  Jan. 10, 2019

(51) Int. Cl.
*A61B 17/80* (2006.01)
*A61B 17/56* (2006.01)

(52) U.S. Cl.
CPC .......... *A61B 17/8095* (2013.01); *A61B 17/80* (2013.01); *A61B 2017/561* (2013.01); *A61B 2017/564* (2013.01)

(58) Field of Classification Search
CPC .............. A61B 17/809; A61B 17/8095; A61B 2017/564
See application file for complete search history.

(56) References Cited

U.S. PATENT DOCUMENTS

| | | | |
|---|---|---|---|
| 5,549,612 A * | 8/1996 | Yapp | A61B 17/7059 606/293 |
| 6,086,593 A * | 7/2000 | Bonutti | A61B 17/8004 128/898 |
| 6,544,266 B1 * | 4/2003 | Roger | A61B 17/15 606/281 |
| 8,388,690 B2 | 3/2013 | Singhatat et al. | |
| 8,657,820 B2 * | 2/2014 | Kubiak | A61B 17/1728 606/70 |
| 8,747,474 B2 * | 6/2014 | Ferguson | A61B 17/7059 623/17.16 |
| 9,949,773 B2 * | 4/2018 | Dacosta | A61B 17/8095 |
| 2005/0177245 A1 * | 8/2005 | Leatherbury | A61B 17/7059 623/23.5 |

(Continued)

OTHER PUBLICATIONS

International Search Report and Written Opinion issued in connection with International Patent Application No. PCT/US2016/023721, dated Dec. 8, 2016, 11 pages.

*Primary Examiner* — Anu Ramana
(74) *Attorney, Agent, or Firm* — Duane Morris LLP

(57) ABSTRACT

Various embodiments of wedge plates configured to promote bone growth are disclosed. Generally, a wedge plate comprises a first bone contact section, a second bone contact section, and a wedge section located between the first bone contact section and the second bone contact section. The wedge section is sized and configured to be received within a wedge formed in a bone. The wedge section comprises at least one feature configured to promote bone growth. A bone growth stimulant may be located within the at least one feature.

13 Claims, 3 Drawing Sheets

(56) References Cited

U.S. PATENT DOCUMENTS

2006/0235403 A1* 10/2006 Blain ..................... A61F 2/46
                                                          606/249
2006/0241609 A1   10/2006 Myerson et al.
2009/0177203 A1    7/2009 Reiley
2012/0184959 A1    7/2012 Price et al.
2016/0000486 A1    1/2016 Leduc et al.

* cited by examiner

WEDGE PLATES AND METHODS OF USE

This application is a national phase entry under 35 U.S.C. § 371 of International Patent Application No. PCT/US2016/023721, filed Mar. 23, 2016 which is expressly incorporated herein by reference in its entirety.

FIELD OF THE INVENTION

This disclosure generally relates to systems and methods for osteotomy. More particularly, this disclosure relates to systems and methods for wedge plates used in osteotomies.

BACKGROUND

An osteotomy is a surgical operation whereby a bone is cut to shorten, lengthen, or change the bone's alignment. Osteotomies may be performed to straighten a bone that has healed incorrectly following a fracture, to relieve arthritis pain, or to treat one or more additional issues. Osteotomies are common of the hip and knee bones.

In an osteotomy, a surgeon removes a portion of a first bone, such as a tibia. The portion of bone removed, referred to herein as an osteotomy, is sized and configured to allow reconfiguration of the first bone. The first bone is adjusted to rest an upper portion of the first bone on a second bone, a lower portion of the first bone, and/or on one or more plates inserted into the osteotomy. The bone sections are attached through staples, screws, and the use of one or more wedge plates.

SUMMARY

Various embodiments of wedge plates are disclosed. In one embodiment, a wedge plate comprises a first bone contact section, a second bone contact section, and a wedge section located between the first bone contact section and the second bone contact section. The wedge section is sized and configured to be received within a wedge formed in a bone. The wedge section comprises at least one feature configured to promote bone growth. A bone growth stimulant may be located within the at least one feature.

In another embodiment, a wedge plate comprises a first bone contact section, a second bone contact section, and a wedge section located between the first bone contact section and the second bone contact section. The first bone contact section and the second bone contact section each define at least one hole configured to receive a mounting device. The wedge section is sized and configured to be received within a wedge formed in a bone. The wedge section comprises at least one feature configured to promote bone growth. A bone growth stimulant is located within the at least one feature.

In some embodiments, a method of using a wedge plate is disclosed. The method generally comprises inserting a bone growth stimulant into a feature of a wedge plate, The wedge plate comprises a first bone contact section, a second bone contact section, and a wedge section located between the first bone contact section and the second bone contact section. The feature is located on the wedge section and defines at least one channel configured to promote bone growth. The method further comprises locating the wedge plate at a treatment site such that the wedge section is located within a wedge formed in a bone and attaching the wedge plate to the bone.

BRIEF DESCRIPTION OF THE DRAWINGS

The features and advantages of the present invention will be more fully disclosed in, or rendered obvious by the following detailed description of the preferred embodiments, which are to be considered together with the accompanying drawings wherein like numbers refer to like parts and further wherein.

DETAILED DESCRIPTION

Figure 1:
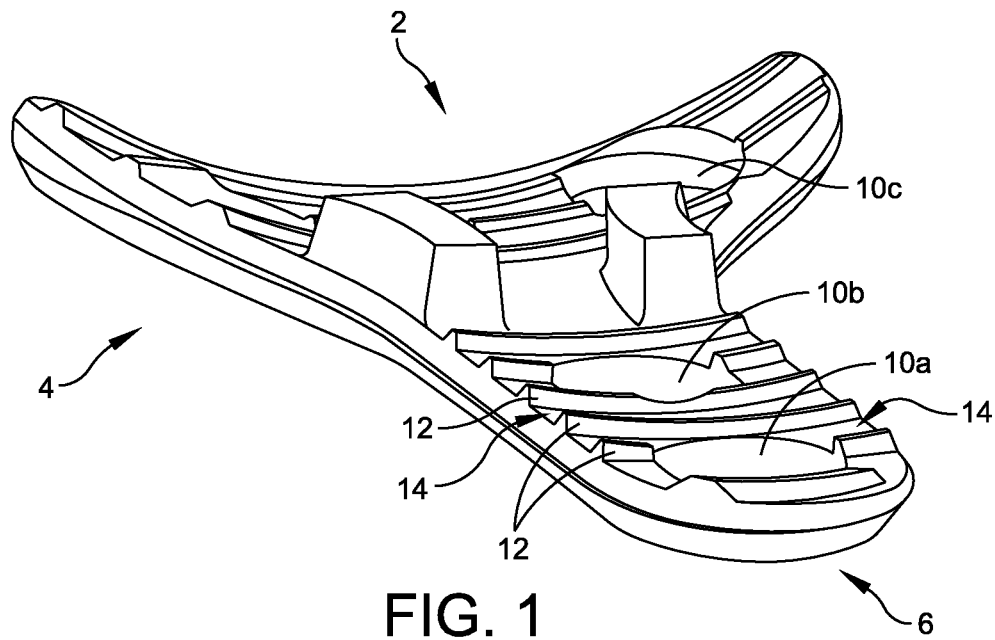
FIG. 1 illustrates one embodiment of a wedge plate configured to promote bone growth across an osteotomy formed in a bone.

The description of the exemplary embodiments is intended to be read in connection with the accompanying drawings, which are to be considered part of the entire written description. In the description, relative terms such as "lower," "upper," "horizontal," "vertical," "proximal," "distal," "above," "below," "up," "down," "top" and "bottom," as well as derivatives thereof (e.g., "horizontally," "downwardly," "upwardly," etc.) should be construed to refer to the orientation as then described or as shown in the drawing under discussion. These relative terms are for convenience of description and do not require that the apparatus be constructed or operated in a particular orientation. Terms concerning attachments, coupling and the like, such as "connected" and "interconnected," refer to a relationship wherein structures are secured or attached to one another either directly or indirectly through intervening structures, as well as both movable or rigid attachments or relationships, unless expressly described otherwise.

The present disclosure generally provides a wedge plate for use in osteotomy surgery. The wedge plate generally comprises a first bone contact section and a second bone contact section for anchoring the wedge plate to a first bone section and a second bone section. The wedge plate further generally comprises a wedge section located between the first and second bone contact sections and configured to support a portion of an osteotomy formed in a bone. The wedge section comprises one or more features for promoting bone growth through the wedge.

Figure 2:
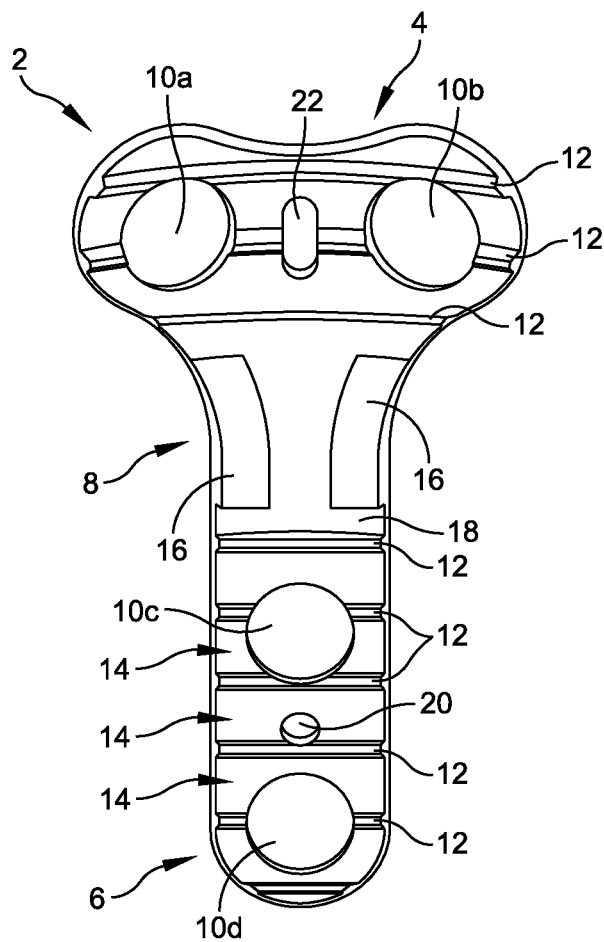
FIG. 2 illustrates a top-down view of the wedge plate of FIG. 1.

FIG. 1 illustrates one embodiment of a wedge plate 2 configured to promote bone growth in an osteotomy. FIG. 2 illustrates a top-down view of the wedge plate 2. The wedge plate 2 comprises a first bone contact section 4 and a second bone contact section 6. A wedge section 8 is located between the first bone contact section 4 and second bone contact section 6. The first bone contact section 4 and the second bone contact section 6 each comprise at least one hole 20, 22 configured to receive a fastener therethrough. One or more fasteners, such as a plate screw, are inserted through the holes 20, 22 to couple the wedge plate 2 to a bone having an osteotomy formed therein. The holes 20, 22 may comprise threaded and/or unthreaded holes. The wedge section 8 comprises at least one support configured to be located between a first bone section and a second bone section and to provide support for the first and second bone sections.

The wedge plate 2 comprises a bone-contact face defined by the first bone contact section 4, second bone contact section 6, and the wedge section 8. The bone-contact face is configured to be placed against a bone having a gap therein, such as, for example, a gap formed during an osteotomy. The wedge plate 2 is secured to the bone by a plurality of mounting devices inserted through one or more of the holes 20, 22. The wedge section 8 is configured to fit within an osteotomy formed in the bone to provide support and maintain a predetermined alignment.

In some embodiments, the wedge plate 2 generally comprises a T-shape. Although a T-shaped wedge plate 2 is generally disclosed herein, it will be recognized that the wedge plate 2 may have any suitable shape, such as, for example, an oval, I-beam, and/or any other suitable shape. In some embodiments guide holes or slots 20, 22 are formed in the wedge plate 2. The guide holes 20, 22 may be configured to guide the wedge plate 2 into position. For example, in some embodiments, the guide holes or slots 20, 22 are configured to receive a k-wire therein. The wedge plate 2 slides over the k-wires to position the wedge plate 2 at a treatment location. In other embodiments, one or more alternative and/or additional guide/fixation devices may be received within the guide holes or slots 20, 22.

In some embodiments, the first bone contact section 4 and the second bone contact section 6 each comprise a plurality of ridges 12. The ridges 12 are configured to contact a bone section and to provide an open space 14 between the ridges 12. The ridges 12 are configured to provide a secure coupling to a bone section to prevent movement of the wedge plate 2 during and after insertion. In some embodiments, one or more spaces 14 between the ridges 12 may be packed with a bone growth stimulator to promote bone remodeling and enhance fusion between bone sections. In some embodiments, the ridges 12 provide contact points with a bone configured to prevent movement of the wedge plate 2 during and after insertion.

The wedge plate 2 comprises one or more features configured to promote bone growth. In one embodiment, one or more wedge features 16 are located in the wedge section 8 of the wedge plate 2. The one or more features 16 are inserted into a space formed in a bone during an osteotomy. The features 16 maintain the bone sections in a predetermined spacing and/or alignment until fusion of the first and second bone sections occurs. In some embodiments, the features 16 comprise at least a first wall 16a and a second wall 16b extending longitudinally along the length of the wedge section 8. The first wall 16a and the second wall 16b are generally parallel and define a channel or cavity 18 therebetween. The first wall 16a and the second wall 16b may be located at opposite edges of the wedge plate 2 and may follow the outer contour of the wedge plate 2. The channel 18 is configured to promote bone growth through the wedge section 8. The channel 18 allows bone ingrowth through the wedge section 8. The channel 18 may be packed with a bone growth stimulator to stimulate remodeling and enhanced fusion of the bone across the osteotomy. The first wall 16a, second wall 16b, and the channel 18 promote bone growth without diminishing the support provided by the wedge section 8.

The first bone contact section 4 of the wedge plate 2 comprises a first hole 10a and a second hole 10b. The first hole 10a and the second hole 10b are horizontally aligned. The first and second holes 10a-10b are configured to couple the wedge plate 2 to an upper bone section. The wedge plate 2 defines a first curved section and a second curved section about each of the respective first and second holes 10a-10b. The first and second curved sections may define, for example, a mouse-eared shape. Those skilled in the art will recognize that the first bone contact section 4 may comprise any suitable shape and any suitable number of holes 10a-10b for coupling to a bone section.

The second bone contact section 6 of the wedge plate 2 comprises a third hole 10c and a fourth hole 10d. The third hole 10c and the fourth hole 10d are longitudinally aligned. The third and fourth holes 10c-10d are configured to couple the wedge plate 2 to a lower bone section. The wedge plate 2 defines an elongate section about the third and fourth holes 10c-10d. In some embodiments, a mounting device, such as a screw, may be inserted into each of the third and fourth holes 10c-10d. In some embodiments, a mounting device may be inserted into only one of the third hole 10c or the fourth hole 10d. Although two holes are illustrated, it will be recognized that the second bone mounting section 6 may comprise any suitable number of holes, such as, for example, one hole, two holes, and/or multiple holes.

Figure 3:
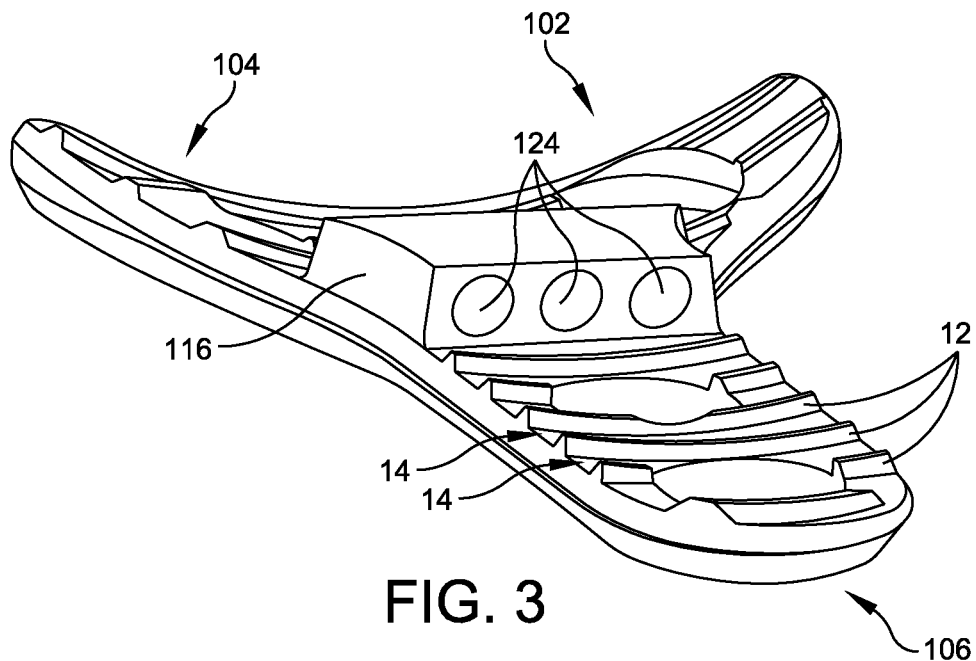
FIG. 3 illustrates one embodiment of a wedge plate having a plurality of holes for promoting bone growth.
Figure 4:
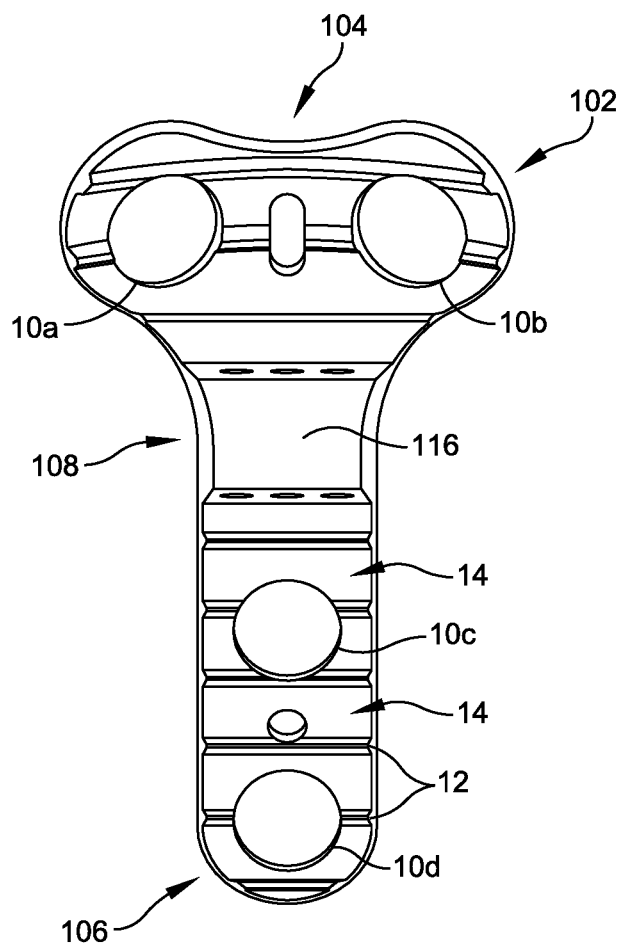
FIG. 4 illustrates a top-down view of the wedge plate of FIG. 3.

FIG. 3 illustrates one embodiment of a wedge plate 102 comprising a wedge block 116 having one or more holes 124 formed therein. FIG. 4 illustrates a top-down view of the wedge plate 102. The wedge plate 102 comprises a first bone contact section 104 and a second bone contact section 106 having a wedge section 108 therebetween. The wedge section 108 comprises a block 116. The block 116 comprises a continuous block extending horizontally across the width of the wedge plate 102. The block 116 may comprise a longitudinal width corresponding to a size of a gap formed in a bone of a patient. The block 116 is sized and configured to be inserted into an osteotomy formed in a bone. The block 116 provides support for the first and second bone sections.

The wedge block 116 comprises one or more through holes 124. The through holes 124 are configured to promote bone growth through the wedge block 116. The holes 124 promote bone ingrowth between the first bone section and the second bone section across the wedge section 108. The through holes 124 may be empty and/or may be partially or fully packed with a bone growth stimulant. The wedge block 116 maintains the bone and/or bone sections in a specific alignment and promotes fusion of the bone through the through holes 124. Although the through holes 124 are shown extending longitudinally along the length of the wedge plate 102, it will be recognized by those skilled in the art that the through holes may extend at any angle through the wedge block 116, such as, for example horizontally and/or diagonally. In some embodiments, the through holes 124 comprise one or more longitudinal slots and/or any other suitable shape.

The wedge plate 102 comprises a plurality of mounting holes 10a-10d and a plurality of ridges 12 similar to the wedge block 2 illustrated in FIGS. 1-2. The plurality of mounting holes 10a-10d are configured to receive mounting devices, such as, for example, screws, therethrough to couple the wedge plate 102 to a bone. The plurality of ridges 12 are configured to contact a bone section on either side of a wedge when the wedge block 116 is inserted into the wedge. The ridges 12 define spaces 14 therebetween. In some embodiments, the spaces 14 may be packed with a bone growth stimulant.

Figure 5:
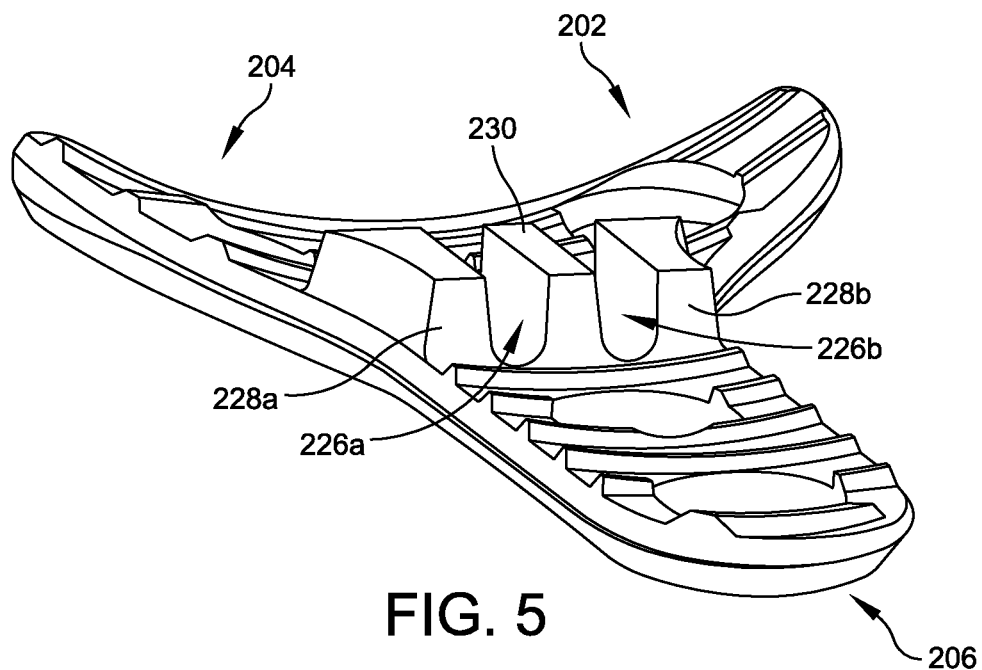
FIG. 5 illustrates one embodiment of a wedge plate having a plurality of channels for promoting bone growth.
Figure 6:
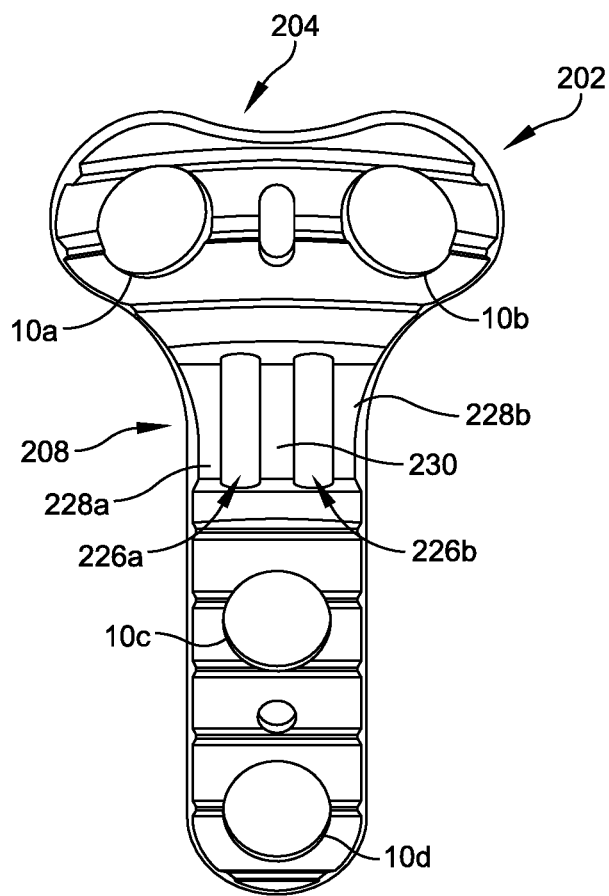
FIG. 6 illustrates a top-down view of the wedge plate of FIG. 5.

FIG. 5 illustrates one embodiment of a wedge plate 202 comprising a wedge section 208 defining a plurality of channels 226. FIG. 6 illustrates a top-down view of a bone-contact surface of the wedge plate 202. The wedge plate 202 comprises a first bone contact section 204 and a second bone contact section 206 coupled by a wedge section 208. The wedge section 208 comprises a wedge support 216. The wedge support 216 comprises a first side wall 228a, a second side wall 228b, and a middle wall 230. The first side wall 228a and the middle wall 230 define a first channel 226a therebetween. Similarly, the middle wall 230 and the second side wall 228b define a second channel 226b therebetween. The channels 226a, 226b are configured to promote bone growth, for example, by allowing bone to grow across and through the wedge section 208. The wedge support 216 is sized and configured to be inserted into an osteotomy formed in a bone. In some embodiments, the first channel 226a and/or the second channel 226b may be packed with a bone growth stimulant to further promote bone remodeling and enhance fusion of the bone. Although the first channel 226a and the second channel 226b are illustrated as longitudinal channels, it will be recognized by those skilled in the art that side walls 228a, 228b and one or more middle walls 230 may be arranged to provide one or more channels extending in any direction, such as, for example, horizontally and/or diagonally.

The wedge plate 202 comprises a plurality of mounting holes 10a-10d and a plurality of ridges 12 similar to the wedge plate 2 illustrated in FIGS. 1-2. The mounting holes 10a-10d are configured to receive a mounting device, such as, for example, a screw, therethrough. The mounting devices secure the wedge plate 202 to a first bone section and a second bone section. The plurality of ridges 12 are configured to contact a bone section. The ridges 12 define spaces 14 therebetween. In some embodiments, the spaces 14 may be packed with a bone growth stimulant.

The foregoing embodiments generally disclose wedge plates comprising one or more features to promote bone growth across an osteotomy. The one or more features are configured to promote bone growth between a first bone section and a second bone section through a wedge section of a wedge plate. In some embodiments, the wedge plate comprises a first bone contact section, a second bone contact section, and a wedge section located between the first bone contact section and the second bone contact section. The wedge section is sized and configured to be received within a wedge formed in a bone. The wedge section comprises at least one feature configured to promote bone growth.

In some embodiments, the at least one feature comprises a first side wall and a second side wall spaced apart from the first side wall. The first and second side walls define a channel therebetween.

In some embodiments, the first side wall and the second side wall extend longitudinally across the wedge section.

In some embodiments, the first side wall and the second side wall extend horizontally across the wedge section.

In some embodiments, the at least one feature comprises a first side wall, a second side wall spaced apart from the first side wall, and a middle wall located between the first side wall and the second side wall. The first side wall and the middle wall define a first channel therebetween. The second sidewall and the middle wall define a second channel therebetween. The first channel and the second channel are configured to receive bone ingrowth.

In some embodiments, the first side wall, the second side wall, and the middle wall extend longitudinally across the wedge section.

In some embodiments the first side wall, the second side wall, and the middle wall extend horizontally across the wedge section.

In some embodiments, the at least one feature comprises a wedge block having at least one hole formed therethrough.

In some embodiments, the at least one hole extends longitudinally from a first side of the block to a second side of the block.

In some embodiments, the at least one hole extends horizontally from a first side of the block to a second side of the block.

In some embodiments, the first bone contact section and the second bone contact section each define at least one hole configured to receive a mounting device therethrough.

In some embodiments, the feature is configured to receive a bone growth stimulant therein.

In another embodiment, a wedge plate comprises a first bone contact section, a second bone contact section, and a wedge section located between the first bone contact section and the second bone contact section. The first bone contact section and the second bone contact section each define at least one hole configured to receive a mounting device. The wedge section is sized and configured to be received within a wedge formed in a bone. The wedge section comprises at least one feature configured to promote bone growth. A bone growth stimulant is located within the at least one feature.

In some embodiments, the at least one feature comprises a first side wall and a second side wall spaced apart from the first side wall, the first and second side walls defining a channel therebetween.

In some embodiments, the first side wall and the second side wall extend longitudinally across the wedge section.

In some embodiments, the first side wall and the second side wall extend horizontally across the wedge section.

In some embodiments, the at least one feature comprises a first side wall, a second side wall spaced apart from the first side wall, and a middle wall located between the first side wall and the second side wall. The first side wall and the middle wall define a first channel therebetween. The second sidewall and the middle wall define a second channel therebetween. The first channel and the second channel are configured to receive bone ingrowth.

In some embodiments, the at least one feature comprises a wedge block having at least one hole formed through the block.

In some embodiments, a method of using a wedge plate is disclosed. The method generally comprises inserting a bone growth stimulant into a feature of a wedge plate, The wedge plate comprises a first bone contact section, a second bone contact section, and a wedge section located between the first bone contact section and the second bone contact section. The feature is located on the wedge section and defines at least one channel configured to promote bone growth. The method further comprises locating the wedge plate at a treatment site such that the wedge section is located within a wedge formed in a bone and attaching the wedge plate to the bone.

In some embodiments, the wedge plate is attached to the bone by one or more mounting devices inserted through a plurality of holes formed in the first bone contact section and the second bone contact section of the wedge plate.

Although the subject matter has been described in terms of exemplary embodiments, it is not limited thereto. Rather, the appended claims should be construed broadly, to include other variants and embodiments, which may be made by those skilled in the art.

What is claimed is:
1. A wedge plate, comprising:
a first bone contact section;
a second bone contact section, wherein the first bone contact section and the second bone contact section define a bone-contact surface;

a plurality of ridges extending from the bone contact surface, wherein the plurality of ridges define one or more spaces configured to receive a bone growth stimulant therein; and a wedge section located between the first bone contact section and the second bone contact section and extending from the bone-contact surface, wherein the wedge section is sized and configured to be received within a wedge formed in a bone, and wherein the wedge section comprises a first side wall comprising a first outer surface and a first inner surface and a second side wall comprising a second outer surface and a second inner surface spaced apart from one another with a middle wall comprising a first middle surface and a second middle surface located between the first side wall and the second side wall, wherein the first side wall and the middle wall define a first channel comprising a first continuous surface defined by the first inner surface and a first channel surface and the second side wall and the middle wall define a second channel comprising a second channel surface defined by the second inner surface and the second middle surface, wherein the first channel and the second channel are configured to receive and promote bone ingrowth, wherein the first side wall, the second side wall, and the middle wall extend in a longitudinal direction and the first channel surface and the second channel surface are continuous in the longitudinal direction.

2. The wedge plate of claim 1, wherein the first side wall and the second side wall extend longitudinally across the wedge section.

3. The wedge plate of claim 2, wherein the wedge section comprises a wedge block having at least one hole defined longitudinally from a first side of the block to a second side of the block formed therethrough.

4. The wedge plate of claim 2, wherein the first bone contact section and the second bone contact section each define at least one hole configured to receive a mounting device therethrough.

5. The wedge plate of claim 1, wherein the first side wall and the second side wall extend horizontally across the wedge section.

6. The wedge plate of claim 1, wherein the first side wall, the second side wall, and the middle wall extend longitudinally across the wedge section.

7. The wedge plate of claim 1, wherein the first side wall, the second side wall, and the middle wall extend horizontally across the wedge section.

8. The wedge plate of claim 1, wherein the wedge section comprises a wedge block having at least one hole defined horizontally from a first side of the block to a second side of the block.

9. The wedge plate of claim 1, wherein the wedge section is configured to receive a bone growth stimulant therein.

10. The wedge plate of claim 1, wherein the first bone contact section extends in the longitudinal direction and the second bone contact section extends transverse to the longitudinal direction with the wedge section therebetween such that the wedge plate comprises a T-shape.

11. The wedge plate of claim 10, wherein the first outer surface and the second outer surface are curved and generally extend away from each other as the first side wall and the second side wall approach the second bone contact section.

12. The wedge plate of claim 1, wherein the first inner surface and the first middle surface meet at a bottom surface of the first channel.

13. The wedge plate of claim 12, wherein the bottom surface is curved in a direction from the first side wall to the middle wall.

* * * * *